United States Patent [19]

Hasegawa et al.

[11] Patent Number: 5,243,666
[45] Date of Patent: Sep. 7, 1993

[54] STATIC-IMAGE SIGNAL GENERATION APPARATUS USING FUZZY THEORY

[75] Inventors: Jun Hasegawa, Hino; Akihiko Yajima, Kunitachi; Masao Uehara, Hachioji; Masahiko Sasaki, Hachiji; Katsuyuki Saito; Akinobu Uchikubo, both of Hachioji; Takehiro Nakagawa, Hachiji; Shinji Yamashita, Hachioji; Katsuyoshi Sasagawa, Shirakawa, all of Japan

[73] Assignee: Olympus Optical Co., Ltd., Tokyo, Japan

[21] Appl. No.: 800,906

[22] Filed: Oct. 31, 1990

[30] Foreign Application Priority Data

Nov. 1, 1989 [JP] Japan .................................. 1-286471

[51] Int. Cl.5 .............................................. G06K 9/36
[52] U.S. Cl. ........................................ 382/41; 358/98; 382/6; 382/14; 395/3
[58] Field of Search .................. 382/6, 14, 15, 59, 65; 358/105, 98; 395/61, 3; 356/23; 354/62

[56] References Cited

U.S. PATENT DOCUMENTS

| | | | |
|---|---|---|---|
| 4,462,540 | 10/1990 | Tsujiuchi et al. | 382/1 |
| 4,910,590 | 3/1990 | Gilles et al. | 382/6 |
| 4,984,256 | 1/1991 | Buckley | 382/14 |
| 5,067,160 | 11/1991 | Omata et al. | 382/1 |
| 5,123,057 | 6/1992 | Verly et al. | 382/14 |
| 5,157,732 | 10/1992 | Ishii et al. | 382/1 |

Primary Examiner—Joseph Mancuso
Attorney, Agent, or Firm—Armstrong, Westerman, Hattori, McLeland & Naughton

[57] ABSTRACT

A movement amount detected by a movement detection circuit on the basis of an image signal corresponding to an object image is input to a minimum value detection circuit. This detection circuit sets an operation time for the detection of the minimum value by using fuzzy inference on the basis of the movement amount and the gradient amount of the movement. An image signal corresponding to the smallest movement amount in this operation time is retained in a freeze memory. In this case, the operation time is set by fuzzy inference by using the movement amount and the gradient amount as factors for fuzzy inference so that the operation time can be set automatically to a time suitable for obtaining static images possessing a small amount of movement.

19 Claims, 10 Drawing Sheets

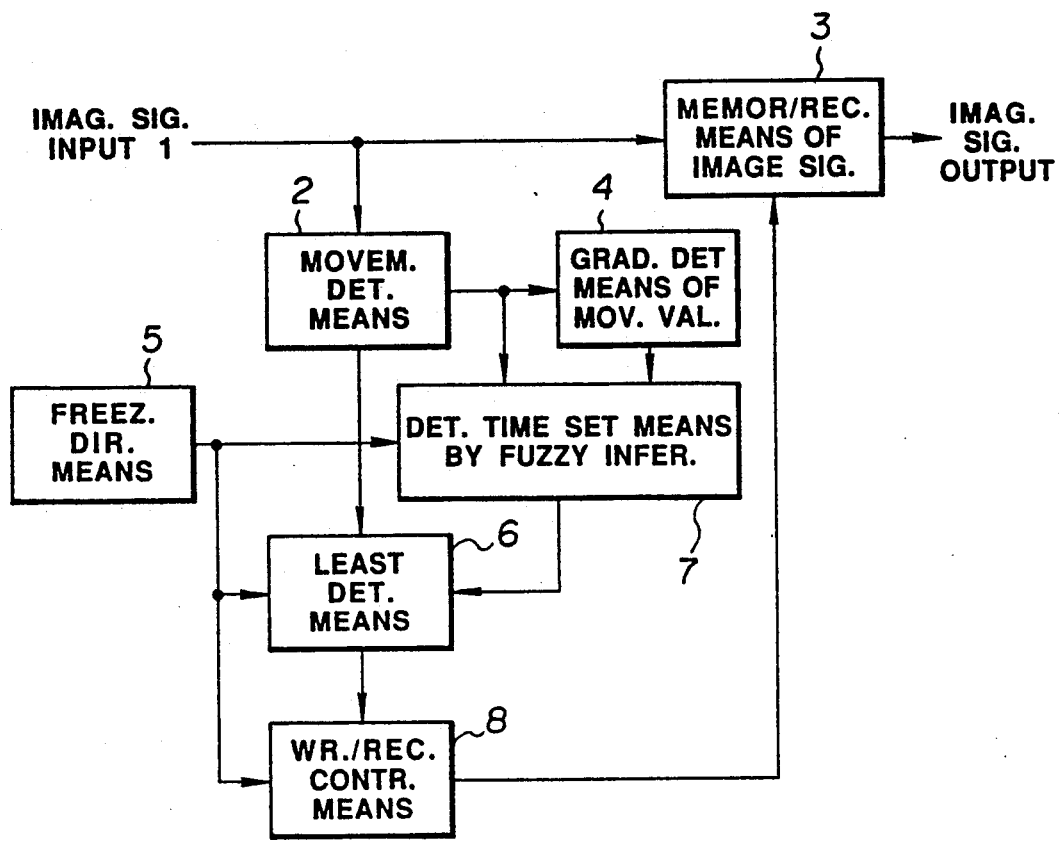
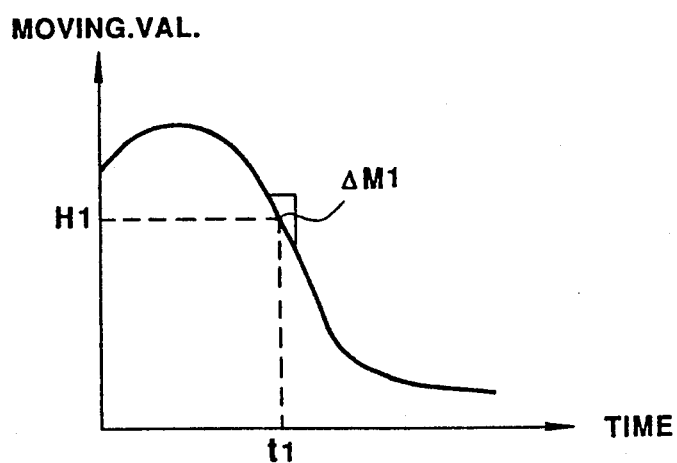

RULE a

RULE b

RULE c

RULE d

RULE e

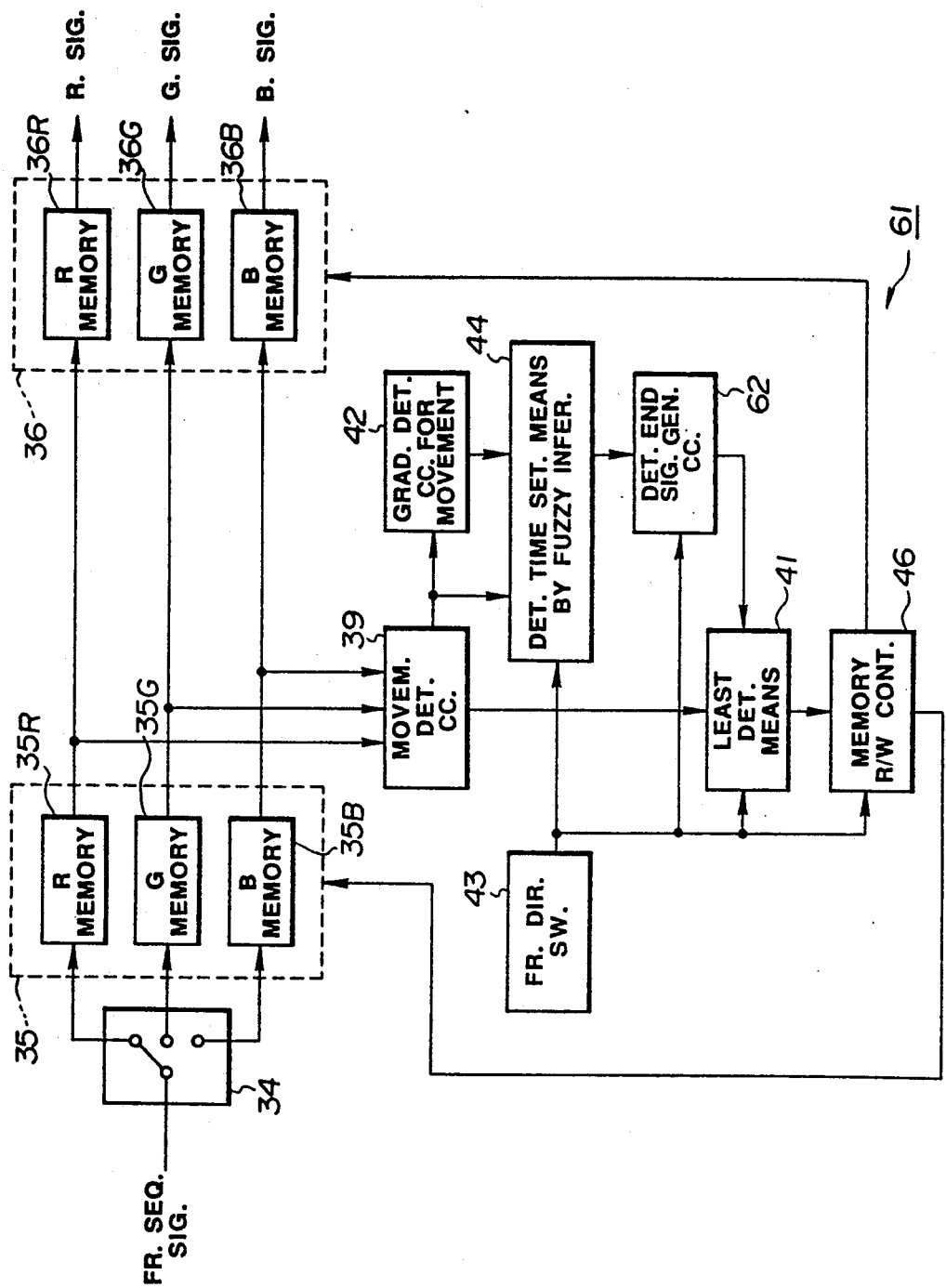

STATIC-IMAGE SIGNAL GENERATION APPARATUS USING FUZZY THEORY

BACKGROUND OF THE INVENTION

1. Field of the Invention

The present invention relates to a static-image signal generation apparatus for obtaining static images having a small amount of image blur by using fuzzy theory.

2. Description of the Related Art

There has previously been known an apparatus that allows image signals to be recorded on a magnetic tape or magnetic disk or to be stored in CCD memory, MOS memory, magnetic bubble memory, or storage devices such as IC memory, and allows the image to be displayed. As an apparatus for specifically obtaining static images, examples of the prior art which are disclosed in Japanese Patent Laid-Open Nos. 49-52912 and 54-910510 have been known. In addition, an electrophotographic camera of the same type as above which is capable of regeneration immediately after photo-taking and capable of taking a photography again, is disclosed in Japanese Patent Laid-Open No. 57-44374.

However, in these apparatus, no small number of cases where the movement of an object is fast in comparison with the shutter speed since recording or storage is performed by pressing the release button, or where image blur occurs in photo-taken static images owing to the fact that an image pickup device moves after shutter operation, so-called camera-shake, and the image must be photographed again. For example, when a fast-moving object is photographed by using a device of an interlaced scanning type as an image pickup device, a drawback arises in that flickering occurs since different images are recorded from field to field, and thus an image which is extremely difficult to see is obtained.

In relation to this drawback, an apparatus is disclosed in U.S. Pat. No. 4,272,787 which is arranged to detect the movement of an object and perform frame freeze when the object is not moving and perform field freeze when the object is moving in order to prevent the interfield flickering at static image storage time. However, since this apparatus field-freezes automatically when the photographed object is moving, this apparatus has a problem in that its resolution in the perpendicular direction deteriorates as regards a moving object.

In recent years, with the advancement of solid-state image pickup technology, pixels have been formed having a high density and chips have been miniaturized, with the result that an endoscope has been developed in which a solid-state image pickup device is mounted at the front end, i.e., an electronic endoscope. This device is inserted into a body cavity and used to observe places to be examined. It has the function of recording the observation image of such place. Not only the observation function, but the quality of the image is very important and exerts a major influence on the diagnosis of the place to be examined. Accordingly, in recording, an operator of the endoscope freezes the image of the place to be examined several times while a patient is made still, selects a most appropriate image as a record image, and records static images in a photo-taking apparatus and a video printer for a monitor image, a still video floppy device, and so on. However, even if a patient is made still, a place to be examined may move in no small amount as long as it is a living body being observed. In order to eliminate an image blur caused by this movement, a problem in that freezing must be performed many times arises.

The deterioration of a record image due to the movement of an object occurs differently depending upon the type of image pickup device and the image pickup method. For example, if a frame transfer type CCD (hereinafter referred to as an FT type CCD) is used as an image pickup device, the movement of an object in an exposure period causes an image blur. If interlaced scanning is performed by using an interline type CCD (hereinafter referred to as an IT type CCD), flickering resulting from the difference in inter-field images occurs in addition to the image blur caused by the movement of an object during the exposure period. In a so-called color frame sequence method in which a monochrome CCD is mounted in the front end of it and illumination light is made into, for example, RGB sequential light, in order to make the size of an endoscope smaller, since images of each of the primary color of RGB, which are photographed chronologically in sequence, are simultaneously displayed, a problem arises, namely, the movement of an object causes a deviation in color when an object is displayed—a so-called color deviation.

To solve the above-described problem, an apparatus has been proposed, by means of which image blur (color deviation) with respect to image signals input within a certain specific period is detected, and an image signal possessing the smallest amount of image blur is displayed on a monitor, etc. as a static image, rather than a static image being displayed on a monitor, etc. at the same time the freezing function works.

However, when a body cavity is observed by means of an endoscope device and the static images of the observed images are recorded by the device, an observation image of a large intestine moves scarcely, an observation image of bronchus moves slowly back and forth at each breathing (when observed by a directly observing type endoscope), and an observation image of a stomach moves peristaltically, and an observation image of an esophagus moves fast because of the respiration of esophagus and pulsation. The amount of movement differs depending upon the difference in the angle of view of each endoscope even at the same observation place. Therefore, the following problems exist. If the detection time for a minimum value is fixed to be constant, the detection time becomes insufficient for a fast-moving image. The detection time is left over for a scarcely moving image, and the next action cannot be performed until the set time is finished.

For this reason, this assignee has proposed an apparatus in Japanese Patent Laid-Open No. 63-286322, in which a minimum value detection means that detects a minimum value of the amount of movement from a movement detection means and a detection time setting means that sets the operating time of this minimum value detection means are disposed so that an image having a smallest amount of movement in a detection time which can be set to any can be stored or recorded.

According to this example of the prior art, an image having a smallest amount of movement is least in a set detection time can be stored or recorded. However, if the detection time for a minimum value is fixed to be constant, the detection time becomes insufficient for a fast-moving image. Conversely, the detection time is left over for a scarcely moving image, and a problem arises in that the next action cannot be performed until the set time is finished.

In addition, even if a detection time is changed for the movement of individual observation places, when movement characteristics vary, for example, the movements are greater or smaller than was expected, a problem occurs in that the detection time is not an appropriate time.

SUMMARY OF THE INVENTION

An object of the present invention is to provide a static-image signal generation apparatus that performs signal processing by which static images having a small amount of movement concerning the movement of an object can be obtained in different situations.

Another object of the present invention is to provide a static-image signal generation apparatus that performs signal processing by which an appropriate detection time can be set according to the circumstances of the movement of an object.

In the present invention, an image signal 1, which is input as shown in the coneceptual figure of FIG. 1, is input to a movement detection means 2. The amount of movement such as image deviation or color deviation of this image signal 1 is detected in sequence. This image signal 1 is also input to an image signal storage/record means 3.

The output of the movement detection means 2 is input to a gradient detection means 4 for detecting the gradient of the movement amount, in which means 4 the gradient amount of movement amount (an inclination of the amount of movement in a very small period) which are input sequentially is detected. The output of the movement detection means 2 is input to a minimum value detection means 6 operated by an image freeze instruction means 5, in which means 5 an image signal possessing the smallest movement amount in a period set by a detection time setting means 7 using fuzzy inference is detected.

To the above detection time setting means 7, a movement amount output from the movement detection means 2 and a gradient amount obtained by the gradient detection means 4 are input. A detection time judged to be most appropriate is detected (inferred) by using fuzzy theory on the basis of the movement amount and the gradient amount, and the time is then output to the minimum value detection means 6.

The minimum value detection means 6 detects the smallest movement amount in the detection time and sends a signal for writing/recording an image signal having the smallest movement amount to a writing-/recording control means 8 where a static image having the smallest movement amount is stored/recorded. In the above way, an appropriate detection time is set depending upon a movement amount and a gradient amount. An image having the smallest movement amount and having a small amount of blur in the detection time is stored in the storage/record means 3 so that an image signal having a small amount of blur is output from the storage/record means 3.

These and other objects, features and advantages of the present invention will become clear when reference is made to the following description of the preferred embodiments of the present invention, together with reference to the accompanying drawings.

BRIEF DESCRIPTION OF THE DRAWINGS

FIG. 1 is a conceptual view showing the construction of the present invention;

FIGS. 2 through 9 show a first embodiment of the present invention;

FIG. 2 is a block diagram showing the construction of an endoscope device equipped with the means of the first embodiment;

FIG. 3 is an explanatory view showing the gradient amount of a movement amount determined on the basis of the movement amount;

FIG. 4 is a block diagram showing the construction of a movement detection circuit;

FIG. 5 is a block diagram showing the construction of a minimum value detection circuit;

FIG. 9 is an explanatory view showing a detection time finally determined from the fuzzy rules;

FIG. 10 is a block diagram showing the construction of a second embodiment of the present invention;

DETAILED DESCRIPTION OF THE PREFERRED EMBODIMENTS

Figure 2:
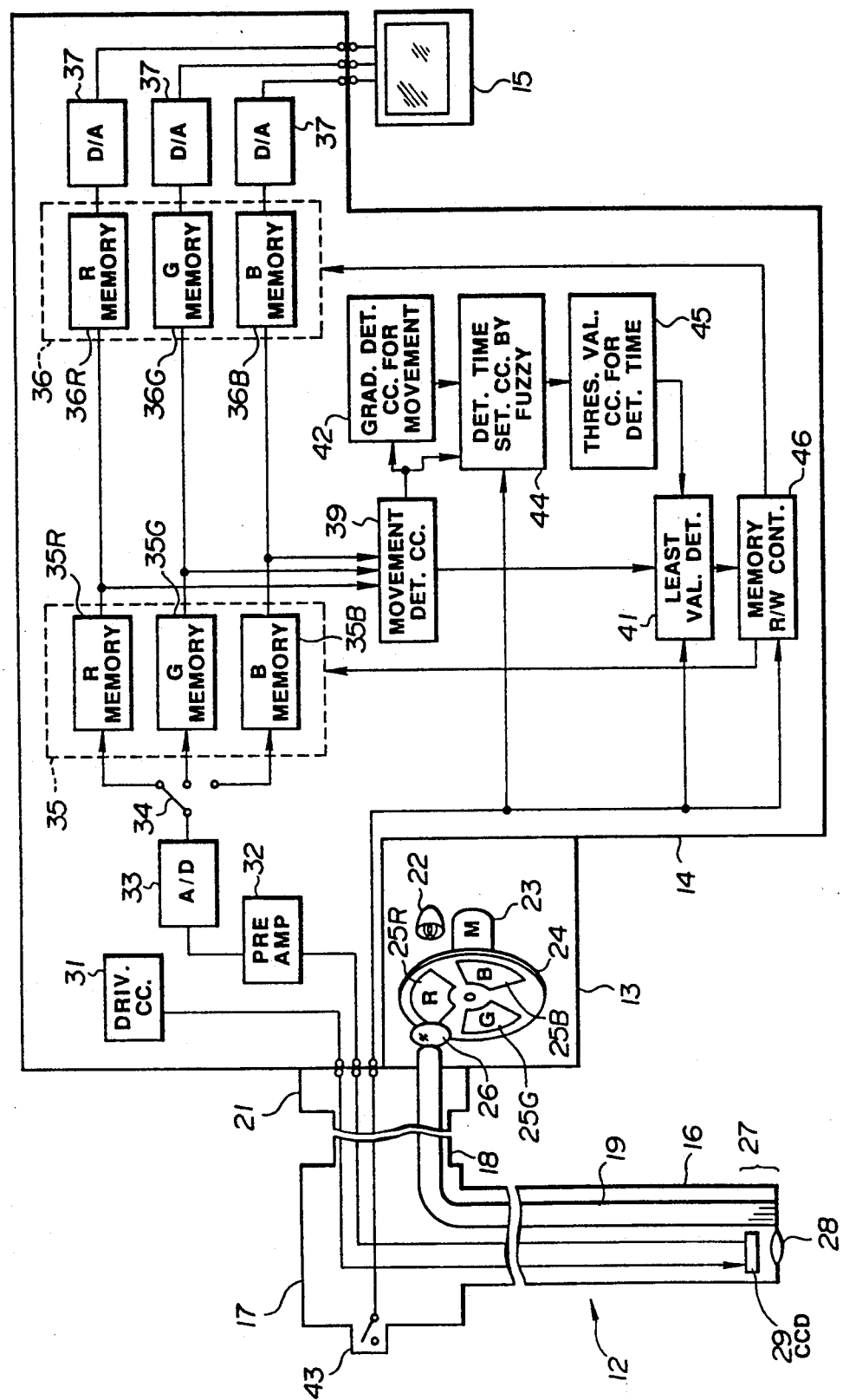

FIG. 2 shows an endoscope device 11, using a RGB frame sequence method, comprising the first embodiment.

This endoscope device 11 comprises an electronic endoscope 12 serving as an image pickup means of a color frame sequence method, a light source apparatus 13 for supplying illumination light of a color frame sequence to the electronic endoscope 12, a static-image signal generation apparatus 14 for performing a usual signal processing on the electronic endoscope 12 and performing a signal processing to obtain static images, and a color monitor 15 on which standard video signals produced by the static-image signal generation apparatus 14 are displayed.

The electronic endoscope 12 consists of a long and narrow insertion section 16, a manipulation section 17 formed on the back end of this insertion section 16, and a universal cable 18 extending outwardly from the side of the manipulation section 17.

A light guide 19 through which illumination light is transmitted is inserted into the insertion section 16 and the universal cable 18. A connector 21 mounted on the back end of the universal cable 18 is mounted on the light source apparatus 13. Thus, illumination light is supplied from this light source apparatus 13.

That is, white illumination light generated by a lamp 22 passes in turn through R, G, and B filters 25R, 25G, and 25B for transmitting red (R), green (G), and blue (B), respectively, thus forming a rotary color filter 24 by causing the light to pass through rotary color filter 24 rotatingly driven by a motor 23. The white illumination light is made into illumination light of R, G, and B. Furthermore, it is condensed by a condenser lens 26 and is made to illuminate the back end of the light guide 19.

The illumination light transmitted through this light guide 19 is forwardly emitted from the tip of the front end section 27 side of the insertion section 16 and is made to chronologically and sequentially illuminate an object, such as an affected part, by the light of each wavelength. The image of the illuminated object is formed on a CCD 29 disposed on a focal point plane by an object lens 28 disposed on the front end section 27.

This CCD 29 photoelectrically converts an optical image and stores it as electric charge that corresponds to this optical image. This electric charge is read out by the application of a drive signal from a drive circuit 31 in the static-image signal generation apparatus 14 and made into an image signal, and is input to a preamplifier 32 in this apparatus 14.

After the image signals are amplified by this preamplifier 32, they are converted to digital signals by an A/D converter 33 and are in turn stored in R, G, and B memories 35R, 35G, and 35B serving as a simultaneous memory 35 through a multiplexer 34.

For example, signals of an image photographed by the CCD 29 under the illumination light after passing through an I filter 251 (I=R, G, or B) are stored in an I memory 351. That is, image signal components (R, G, and B color signals) corresponding to the illumination light of each wavelength are stored in the R memory 35R, the G memory 35G, and the B memory 35B in the simultaneous memory 35. The image signals stored in the R memory 35R, the G memory 35G, and the B memory 35B are read out simultaneously and made into simultaneous color signals and sequentially written in the R memory 36R, the G memory 36G, and the B memory 36B in the freeze memory 36. RGB image signals written in each of the memories 36R, 36G, and 36B in the freeze memory 36 are each converted into analog color signal RGB by a D/A converter 37 and sequentially read out in synchronization with an unillustrated synchronization signal output from a color monitor 15 or a device 14 serving as a display device, which is connected at later stages.

Simultaneous color signals read out from the simultaneous memory 35 are transmitted also to a movement detection circuit 39 which detects the amount of the movement of an object and sends it to a minimum value detection circuit 41.

Also, the output of the movement detection circuit 39 is output to a movement-amount gradient detection circuit (or a movement-amount displacement detection circuit) 42. As shown in FIG. 3, if a movement amount M1 is regarded as a function of time, a gradient amount at time t1 (or a displacement amount) Δ is detected. That is, this gradient amount ΔM1 is detected from the difference in the movement amounts after and before a short time width at time t1.

The movement amount M and the gradient amount ΔM output from the movement detection circuit 39 and the (movement-amount) gradient detection circuit 42 are input to a detection time setting circuit 44 using fuzzy inference which operates in accordance with a freeze instruction signal from a freeze switch 43 for performing freeze instruction. A detection time T is determined by fuzzy inference by using these amounts as factors for inferring the movement amount M and the gradient amount ΔM in this setting circuit 44. The determined detection time T is output to a detection time threshold value circuit 45. When the detection time T falls below a certain value Tth, a signal used to terminate the detection of a minimum value is sent to the a minimum value detection circuit 41.

The minimum value detection circuit 41 detects a minimum value of movement amounts in a period until a detection time termination signal is input. The image signal of which the minimum value is detected is stored in the freeze memory 36 (thereafter, writing is inhibited). A signal is sent to a memory R/W controller 46 so that this stored image signal is read out.

The detection time setting circuit 44 using fuzzy inference sequentially outputs a detection time T considered appropriate to a detection time threshold value circuit 45 on the basis of the movement amount and the gradient amount which are input. This threshold value circuit 45 sends a detection enable signal to the minimum value detection circuit 41 until the input detection time T falls below the threshold value Tth at which the movement amount and the gradient amount are judged to be small.

Figure 4:
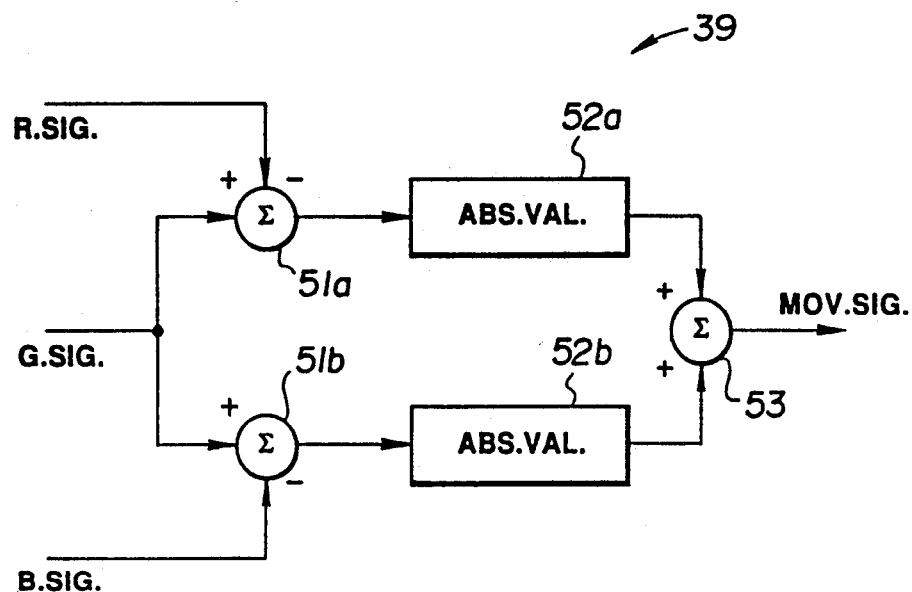

FIG. 4 shows an example of the construction of the movement detection circuit 39.

R, G, and B color signals respectively output serially from the R memory 35R, the G memory 35G, and the B memory 35B in the simultaneous memory 35 are input to subtracters 51a and 51b. R and B color signals are subtracted from the G color signal by respective subtracters 51a and 51b, and difference signals G-R and G-B are output. These difference signals G-R and G-B become values corresponding to the amount of deviation in pixels of G and R color signals (or G and B color signals).

The output signals G-R and G-B of the respective subtracters 51a and 51b are input to absolute value circuits 52a and 52b, respectively, where these signals are converted to absolute values |G-R| and |G-B|. Then, they are accumulatively added by an accumulation adder 53, and a movement signal corresponding to the movement amount (the amount of deviation over time) with respect to one frame of an image photographed in frame sequence is output. For example, generally, the larger the movement amount the larger the value of the movement signal.

Figure 5:
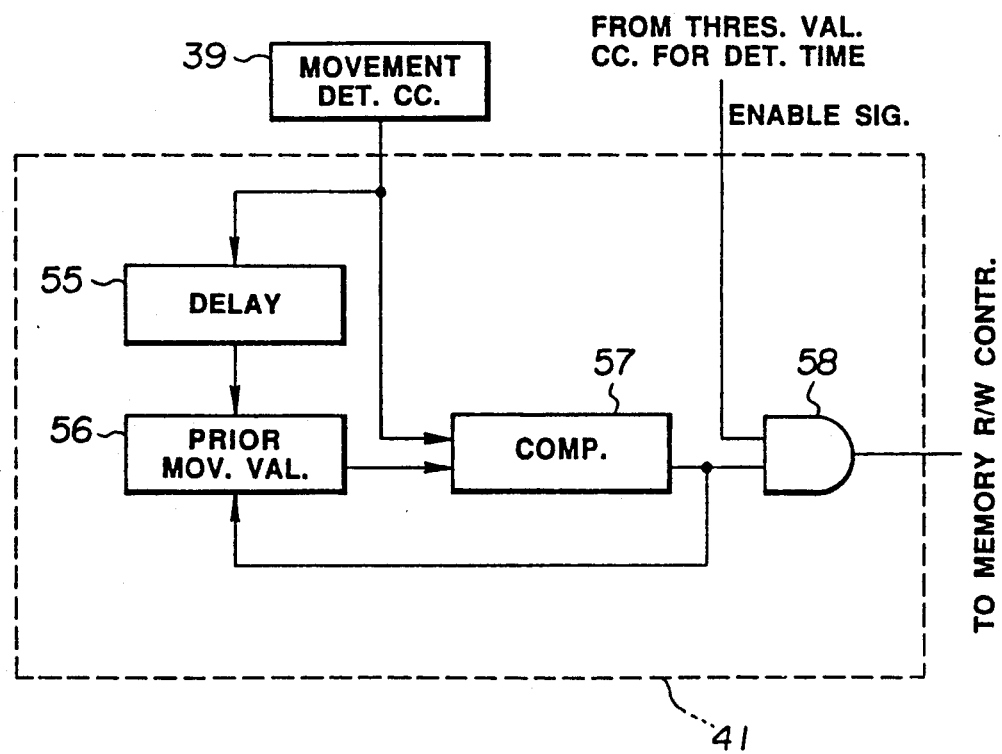

The minimum value detection circuit 41, to which the movement signal of the movement detection circuit 39 is input, is constructed as shown in FIG. 5.

The movement signal is input to a preceding movement signal retaining circuit 56 through a delay circuit 55, and update is controlled by the decision output of a comparator 57. To this comparator 57, the movement signal of the movement detection circuit 39 and the preceding movement signal retained in the preceding movement signal retaining circuit 56 are input. Only when it is determined that the movement signal is smaller than the preceding movement signal, i.e., that the latter image has a smaller amount of movement than the preceding image, an update signal for updating data of the preceding movement signal retaining circuit 56 is output. An update signal for writing the image of the simultaneous memory 35 in the freeze memory 36 is output to the memory R/W controller 46 via an AND gate 58. To this AND gate 58, a detection enable signal for enabling the minimum value detection is input from the threshold value circuit 45. When this enable signal is no longer input and is turned to "L", the gate is closed and update is inhibited. In the above way, an image written immediately before the enable signal is finished is retained as a static image in the freeze memory 36. This image is output on the monitor 15 repeatedly and displayed as a static image.

The delay circuit 55 is designed to delay time so that the next signal output from the movement detection circuit 39 can be input to the preceding movement signal retaining circuit 56 on the basis of the decision output of which the decision of the movement amount with respect to two signals is terminated by the comparator 57.

Figure 6A:
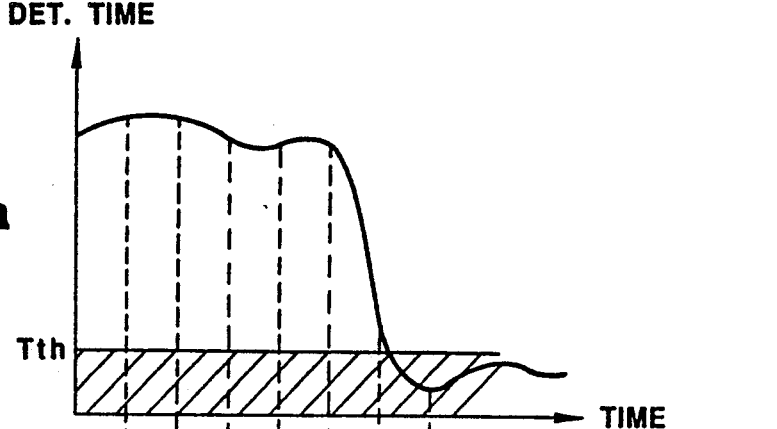
FIGS. 6a-b is an explanatory view showing the circumstances in which a detection time and an image signal are frozen or not frozen.

FIG. 6 shows a detection time output from the detection time setting circuit 44 to the threshold value circuit 45 and the process by which the output of the minimum value detection circuit 41 is controlled in accordance with a detection signal of the threshold value circuit 45 and by which the image is frozen.

Since the detection time T output from the detection time setting circuit 44 is, for example, larger than the threshold value Tth, as shown in FIG. 6, the minimum value detection circuit 41 retains the movement amount m0 of the image signal at time t0, and sends an update signal to the memory R/W controller 46 so that the image signal can be written in the freeze memory 36. Next, the movement amount m1 at time t1 is compared with the above movement amount m0. The image signal having a smaller value is retained (stored) in the freeze memory 36. In this case, since m0 is less than m1, the freeze memory 36 is not updated, and the image signal at time t0 is retained and the value of the movement amount m0 is retained in the minimum value detection circuit 41. In this state, an image signal at time t0 is output from the freeze memory 36.

Figure 6B:
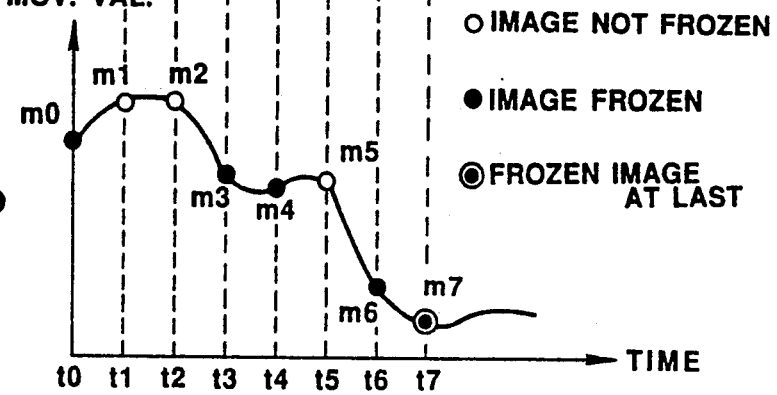

Similarly, since a movement amount m2 is larger than m0 concerning an image signal at time t2, the freeze memory 36 is not updated, and the image signal having the movement amount m0 is retained, and the value of the movement amount m0 is retained in the minimum value detection circuit 41. Similarly, the same processing is performed at t3, t4, . . . . Image signals having a smaller amount of movement are stored (retained) one after the other, and these stored image signals are read out. In the above way, as shown in FIG. 6b, movement amounts m0, m3, m4, m6, . . . are in turn retained in the freeze memory 36, and the retained image signals are read out.

Next, the detection (setting) of a detection time by the detection time setting circuit 44 using fuzzy inference will be explained.

Figure 7A:
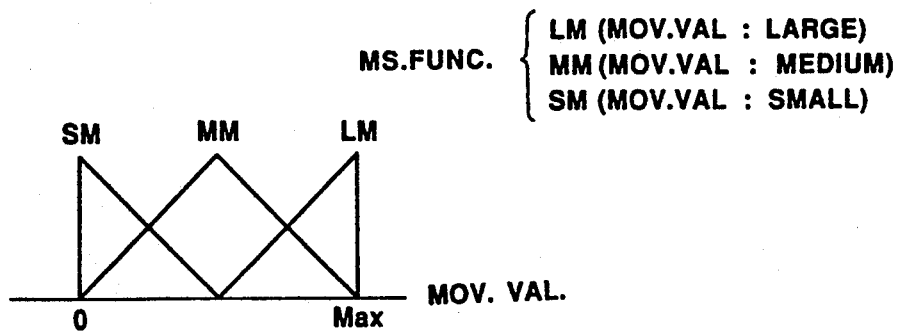
FIGS. 7a-c is an explanatory view showing each membership function for determining a detection time by using fuzzy theory.
Figure 7B:
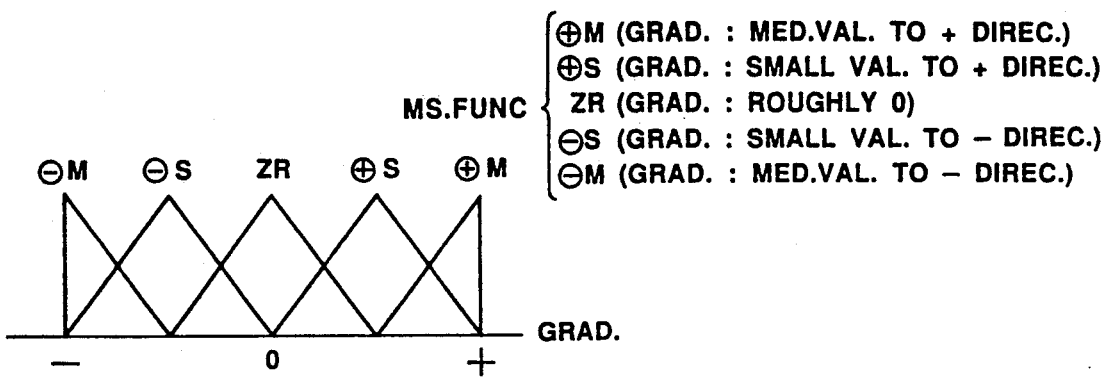
Figure 7C:
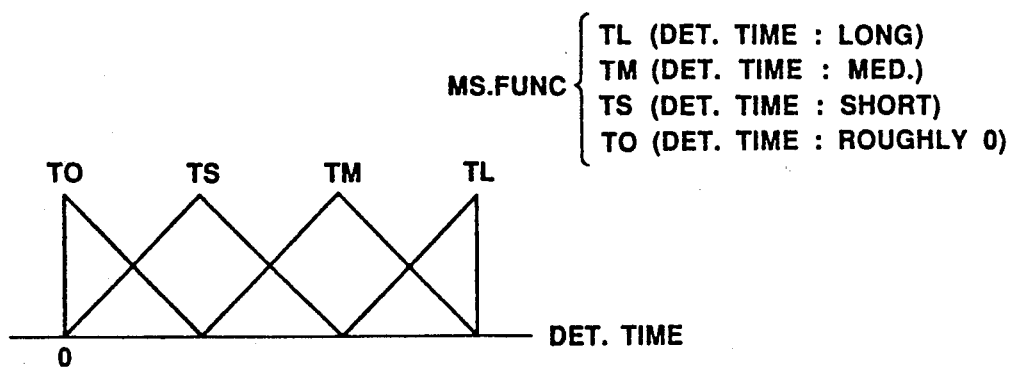

In this first embodiment, each membership function, for example, that for a movement amount, a gradient amount, and a detection time, is set as shown in FIG. 7. The movement amount is expressed by three membership functions, as shown in FIG. 7a. The gradient amount is expressed by the five membership functions of FIG. 7b. The detection time which becomes the following subject matter in correspondence with these membership functions of the preceding subject matter are expressed by four membership functions, as shown in FIG. 7c. These membership functions are associated with the following rules a to e.

Rule a: if the movement amount is large and the gradient amount is in the + direction and large, the detection time is increased.

Rule b: if the movement amount is medium and the gradient amount is in the + direction and small, the detection time is decreased.

Rule c: if the movement amount is small and the gradient amount is approximately zero, the detection time is made approximately zero.

Rule d: if the movement amount is medium and the gradient amount is in the − direction and large, the detection time is decreased.

Rule e: if the movement amount is large and the gradient amount is medium in one direction, the detection time is made medium.

If the above rules a to e are schematically expressed by using the symbols shown in FIG. 5:

Rule a: if the movement amount is LM and the gradient amount is ⊕M, the detection time is made TL.

Rule b: if the movement amount is MM and the gradient amount is ⊕S, the detection time is made TS.

Rule c: if the movement amount is SM and the gradient amount is ZR, the detection time is made TO.

Rule d: if the movement amount is MM and the gradient amount is $\theta$M, the detection time is made TS.

Rule e: if the movement amount is LM and the gradient amount is $\theta$M, the detection time is made TM.

As shown above, to determine the detection time by using the membership functions and rules a to e, if the movement amount is denoted as M1 and the gradient amount is denoted as ΔM1, the degree of matching (values between 0 and 1) with each membership function and the detection time derived from the rules a to e correspond to each other as shown in FIGS. 8a to 8e.

The column on the left in FIG. 8 denotes membership functions of movement amounts, and the center denotes membership functions of the gradient amounts. With these two membership functions as the preceding subject matter, detection times as the following subject matter on the right correspond.

Figure 8A:
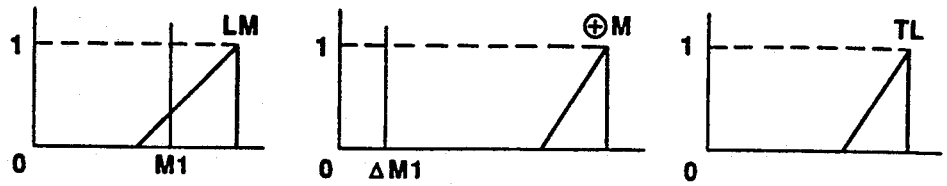
FIGS. 8a-e is an explanatory view showing the membership functions formed into fuzzy rules.
Figure 8B:
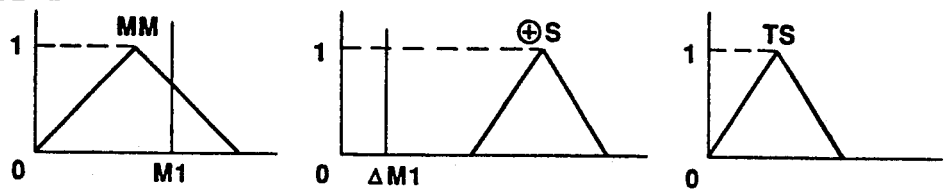
Figure 8C:
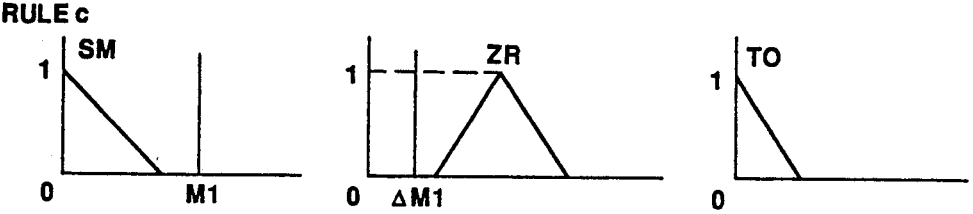
Figure 8D:
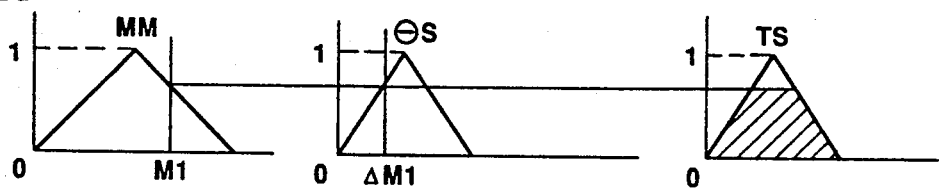
Figure 8E:
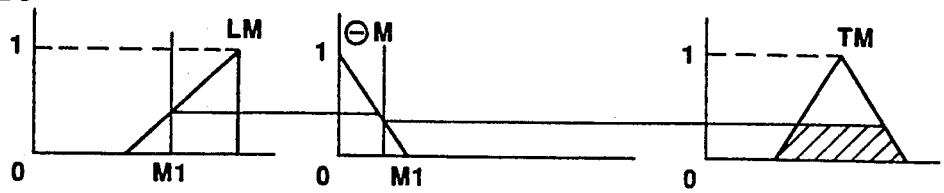

Regarding two membership functions of the preceding subject matter connected by "AND", the value having a smaller degree of matching with the obtained values prescribes the degree of the membership function for the detection time. For example, in FIGS. 8a, 8b, and 8c, the degree of matching in the smaller membership function becomes zero, and it does not become a factor that prescribes the detection time. In FIGS. 8d and 8e, one of the degrees is slightly smaller than the other. The result of inference of the detection times each shown by the shaded portion by this smaller degree is obtained. The magnitude of the detection time is changed depending upon the direction of the gradient amount corresponding to whether an object has a tendency to be moving or to be still.

Figure 9:
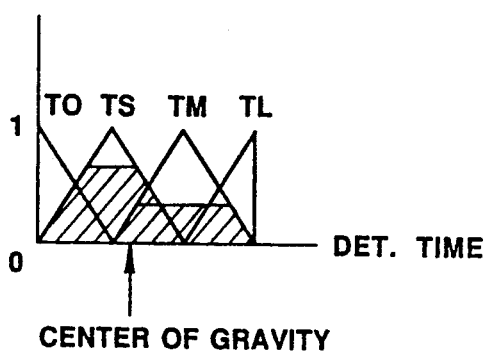

When the results of the inference obtained by rules a to e of FIGS. 8a to 8e are overlapped (combined by OR), the position of the detection time at which the area of the shaded portion of the membership function shown in FIG. 9 is halved, i.e., the center of gravity, becomes the detection time of the final inference value.

The detection time obtained by the detection time setting circuit 44 using fuzzy inference is input to the detection time threshold value circuit 45, as described above. As shown in FIG. 6, when the detection time is greater than the threshold value (time t0 to t6), the minimum value detection circuit 41 is caused to operate. When the detection time falls below a threshold value as at time t7, the image signal which is less than this threshold value and of which a minimum value is detected is output from this apparatus 14 as a final image signal.

According to the first embodiment, the detection time obtained by fuzzy inference can be set to a detection time such that the smaller the movement amount and the gradient amount, the smaller the value that the detection time assumes. Therefore, a setting can be made more appropriately than in a case where the detection time is preset, and a static image having a small amount of movement can be obtained.

That is, the detection time is set on the basis of the gradient amount as well as the movement amount. In the case of an image having a tendency to be moving (the gradient amount is +), a large (lengthy) detection time is obtained. In the case of an image having a tendency to be still, a small (short) detection time is obtained. Consequently, the detection time can be set to an appropriate detection time automatically, depending upon the circumstances of an image, and a freeze image having a small amount of movement can be obtained by the detection time.

As a result, the drawbacks of the prior art in that a final static image cannot easily be obtained due to a lengthily set detection time or a static image having a small amount of movement cannot be obtained due to too short of a detection time can be eliminated.

In this embodiment, the output of the detection time setting circuit 44 is input to the threshold value circuit 45 so that the detection of a minimum value is terminated when the detection time T determined by the detection time setting circuit 44 is the threshold value Tth or smaller. However, the provision of the threshold value circuit 45 can be omitted since if the characteristics of a membership function are set so that the detection time T determined by the detection time setting circuit 44 becomes smaller than a cycle (a time interval of one frame/field, etc.; not necessarily a constant time interval) for the detection of movement, the detection time is finished before the next minimum value is detected when this detection time is reached.

FIG. 10 shows the second embodiment of the present invention.

In the first embodiment, the threshold value circuit 45 is disposed to terminate the detection of a minimum value. In a static-image signal generation apparatus 61 of the second embodiment, a detection termination signal generation circuit 62 is disposed so that a freeze operation is forcibly performed even if the detection time does not fall below a threshold value.

Figure 11:
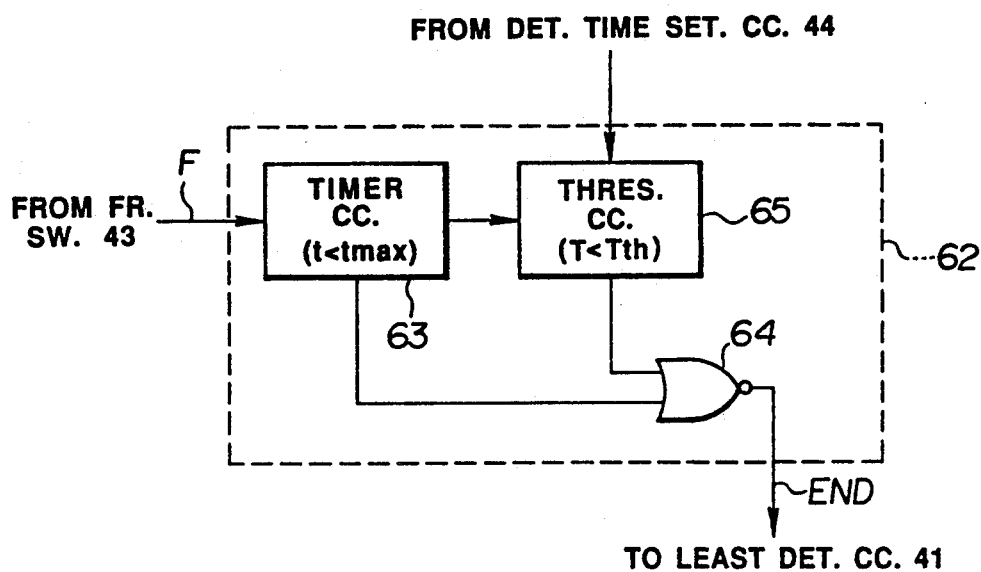
FIG. 11 is a concrete configurational view of a detection termination signal generation circuit in the second embodiment.

The arrangement of the detection termination signal generation circuit 62 is shown in FIG. 11. A freeze (instruction) signal F from the freeze switch 43 is input to the timer circuit 63, causing the timer circuit 63 to be actuated. The timer circuit 63 compares the maximum time tmax of the detection time for the minimum value with a time t elapsed after the timer is turned on. When t>tmax, the timer circuit 63 outputs a maximum time detection signal of "1".

The threshold value 65, to which the detection time T from the detection time setting circuit 44 is input, compares the detection time T of the detection time setting circuit 44 with the threshold value Tth. When T≦Tth, a detection signal of "1" is output; when t>Tth, "0" is output.

The outputs of the threshold value 65 and the timer circuit 63 are input to a NOR circuit 64. If either a maximum time tmax of the minimum value detection time or a time smaller than the threshold value Tth is input to the NOR circuit 64, a termination signal END (a signal that the enable signal of FIG. 5 is turned to "L") is sent to the minimum value detection circuit 41.

The other parts of the second embodiment are constructed similarly to those of the first embodiment. They are denoted by like reference numerals, and the explanation thereof is omitted.

Figure 12:
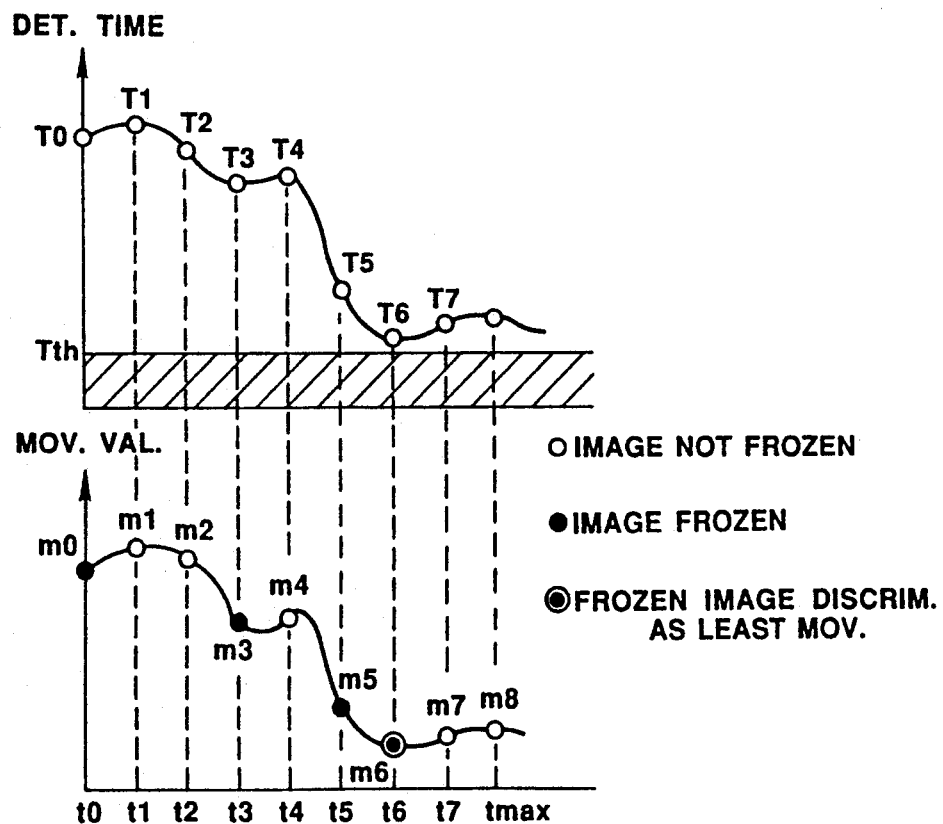
FIG. 12 is an explanatory view showing the circumstances in which a detection time and an image signal are frozen or not frozen in the second embodiment.

FIG. 12 explains the operation of the second embodiment.

When a freeze instruction signal is output from the freeze switch 43 at time t0, the timer circuit 63 is placed in an operating state by this instruction signal F. This instruction signal F also causes the detection time setting circuit 44 to output a detection time T0 to the threshold value circuit 65.

In this state, both the outputs of the timer circuit 63 and the threshold value circuit 45 are "0". The minimum value detection circuit 41 first outputs a signal to the memory R/W controller 46 so as to store image signals at time t0 in the freeze memory 36, and retains a movement amount m0 in the minimum value detection circuit 41.

Next, at time t1, whether or not a detection time T1 from the detection time setting circuit 44 is above the threshold value Tth is determined by the threshold value circuit 65. Also, the timer circuit 63 determines whether or not a time t1-t0 is above the maximum time tmax of the detection time. In the case of FIG. 12, both circuits 65 and 63 output a signal of "0". Hence, the minimum value detection circuit 41 compares the movement amount m1 at time t1 with the movement amount m0 at the previous time t0 and retains the image signal of the smaller value in the freeze memory 36.

In this case, since m0 is less than m1, image signals at time t0 are retained in the freeze memory 36, and the image signals at time t0 are read out from this freeze memory 36. The value of the movement amount m0 is retained in the minimum value detection circuit 41.

The same operation is performed at time t2, t3, ... in sequence. However, when the detection time input to the threshold value circuit 65 does not become a detection time less than the threshold value Tth even if the detection time exceeds the maximum time tmax of the detection time as at time t8, a signal of "1" is output from the timer circuit 63 and passed to the NOR circuit 64, then a minimum value termination signal END is input to the minimum value detection circuit 41. Therefore, in this case, image signals at the minimum value detection time t6 up to time t7 are output as the final static image.

In this second embodiment, a freeze image having a smallest amount of movements within a certain detection time can reliably be obtained, in a case where since a detection time becomes lengthy as a movement amount and the like is large, a desired freeze image cannot be readily obtained.

Figure 13:
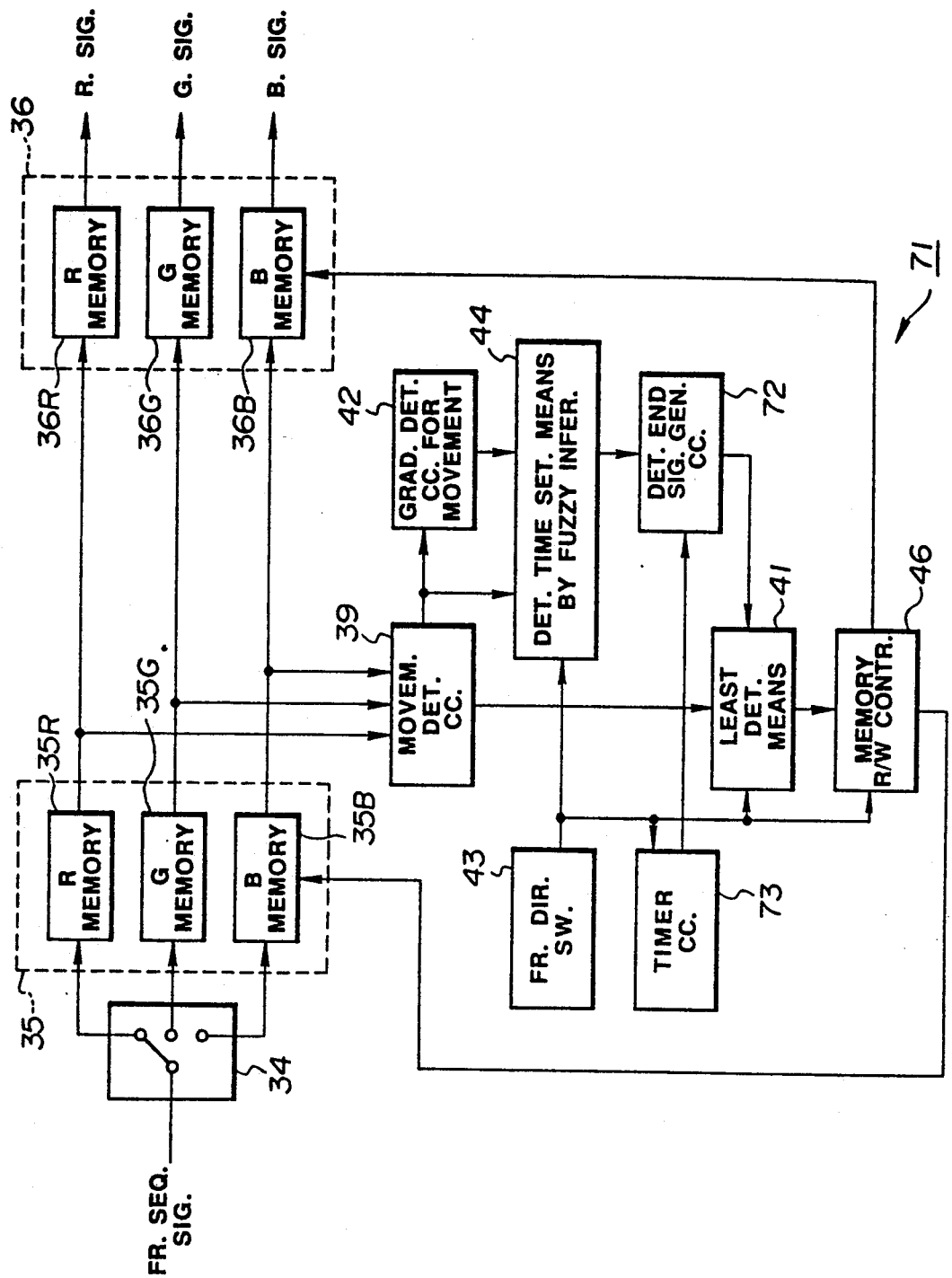
FIG. 13 is a block diagram showing the construction of a third embodiment of the present invention.

FIG. 13 shows a static-image signal generation apparatus 71 of the third embodiment of the present invention.

In this third embodiment, a detection termination signal generation circuit 72 is provided in place of the detection time threshold value circuit 45 as in the first embodiment shown in FIG. 2, and a timer circuit 73 that operates by a freeze instruction signal is provided.

Figure 14:
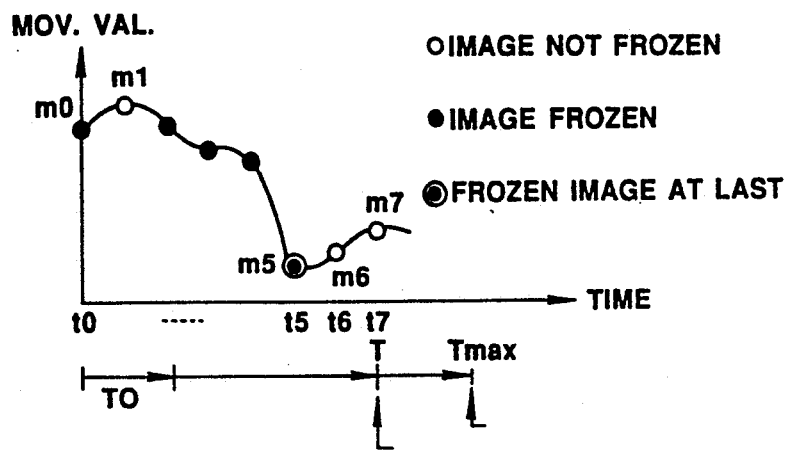
FIG. 14 is a view for explaining the operation of the static-image signal generation apparatus in the third embodiment.

The detection termination signal generation circuit 72 is actuated by a signal from the timer circuit 73. As shown in FIG. 14, at a predetermined time T0, the detection termination signal generation circuit 72 detects the detection time T from the detection time setting circuit 44 so as to control in such a way that an image having a smallest amount of movements within this detection time T is frozen.

The timer circuit 73 is used to control so as to freeze an image having the smallest amount of movements within this predetermined time Tmax when a detection time above the predetermined time Tmax is obtained by fuzzy inference, as shown in FIG. 14.

Therefore, the detection termination signal generation circuit 72 sends a detection signal to the minimum value detection circuit 41 so as to freeze an image having the smallest amount of movement within either the detection time T by fuzzy inference from the detection time setting circuit 44 or the predetermined time Tmax from the timer circuit 73, which is smaller.

In this third embodiment, a time until an image is frozen can be made not too lengthy as in the second embodiment.

Figure 15:
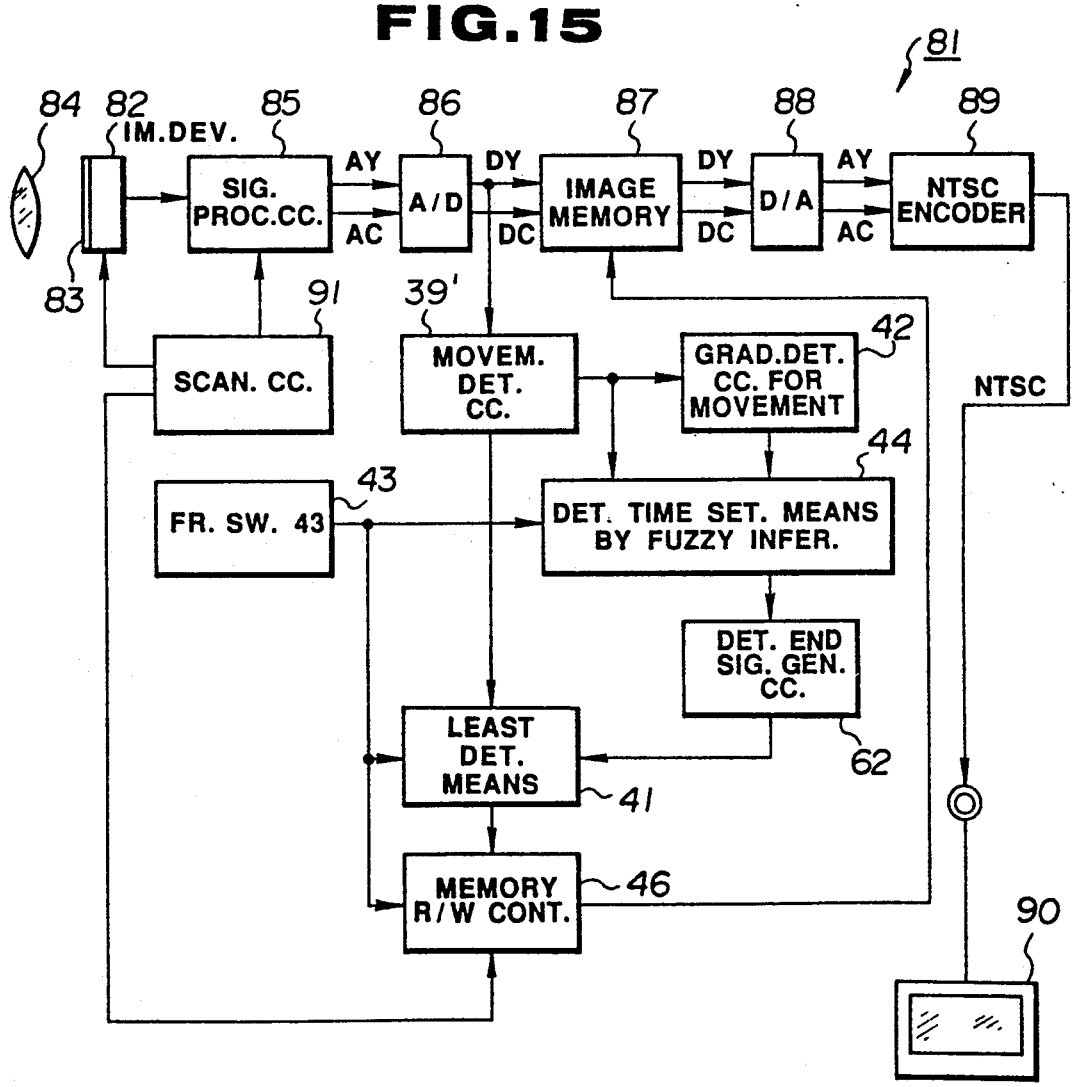
FIG. 15 is a configurational view of an image pickup device equipped with the devices of a fourth embodiment.

FIG. 15 shows an image pickup device 81 comprising the fourth embodiment of the present invention.

In the first to the third embodiments described above, the case of the RGB color frame sequence method was shown. The fourth embodiment involves a color simultaneous image pickup system comprising a mosaic filter 83 employed as an image pickup device 82.

An optical image which is formed on the image pickup device 82 in an image pickup system 84 is photoelectrically converted and input to a signal processing circuit 85. An analog brightness signal AY and an analog color line sequence signal AC obtained by signal processing are converted from analog to digital by an A/D converter 86 and become a digital brightness signal DY and a digital color line sequence signal DC, respectively. The digital brightness signal DY and the digital color line sequence signal DC are written in an image memory 87. Signals DY and DC read out from this image memory 87 are converted from digital to analog by a D/A converter 88 and made into an analog brightness signal AY and an analog color signal AC. These signals are converted to NTSC composite video signals by an NTSC encoder 89, then are displayed on an outside monitor 90.

The above image pickup device 82 is driven by a scanning circuit 91. To the signal processing circuit 85 also, signals of the scanning circuit 91 are input.

The output signal of the A/D converter 86, i.e., the digital brightness signal DY, is input to a movement detection circuit 39'. The output signal of this movement detection circuit 39' is input to the minimum value detection circuit 41 and the movement-amount gradient detection circuit 42. The output of the movement-amount gradient detection circuit 42 is input to the detection time setting circuit 44 using fuzzy inference actuated by the freeze switch 43. The detection time of the detection time setting circuit 44 is, for example, input to the detection termination signal generation circuit 62. The output signal of the detection termination signal generation circuit 62 is input to the minimum value detection circuit 41 where a smallest movement amount until a detection termination signal is input is detected. The output of the minimum value detection circuit 41 is input to the memory R/W controller 46, by means of which the image memory 87 is controlled so as to freeze an image having a smallest amount of movements.

The memory R/W controller 46 reads from/writes to the image memory 87 in synchronization with the output signal of the scanning circuit 91.

In this embodiment, movement detection is performed on the basis of the digital brightness signal DY with above-described arrangement, and freeze control is performed based on the detection amount. As regards the above operation, the sense of vision of the human eyes is taken into consideration and an arrangement may be made so that a movement is detected on the basis of the digital brightness signal DY, so that when it is desired to detect a movement by taking notice of, especially, the color of an object, the movement may be detected by using the digital color signal DC. The movement detection circuit 39' detects a movement on the basis of two digital brightness signals DY having a time difference in one frame/field.

The movement amount detected by the movement detection circuit 39' is detected until the minimum value detection circuit 41 outputs a signal indicating that the smallest amount of movements has been detected. The image of signals which are judged to be the minimum value is displayed on the monitor 90.

Different embodiments may be constructed by combining parts of the embodiments described above.

Many widely different embodiments of the present invention can be made without departing from the spirit and scope thereof, therefore, it is to be understood that this invention is not limited to the specific embodiments thereof except as defined in the appended claims.

What is claimed is:

1. A static-image signal generation apparatus using fuzzy theory, comprising:
    movement detection means that detects the movement amount of an image on the basis of an image signal which is input in correspondence with the image of an object and outputs a movement signal corresponding to said movement amount;
    gradient detection means that detects the gradient of a movement amount on the basis of said movement signal output from said movement detection means;
    minimum value detection means that detects a minimum value of movement amounts on the basis of said movement signal output from said movement detection means;
    static-image specifying means that outputs a static image specifying signal for specifying a static image;
    detection time setting means, actuated by said static image specifying signal, that sets the detection time for a minimum value detection by said minimum value detection means using fuzzy inference as factors for inferring respective outputs of said movement detection means and said gradient detection means; and
    image storage/record means for retaining image signals corresponding to the smallest movement amount detected by said minimum value detection means within said detection time as a static image.

2. A static-image signal generation apparatus as claimed in claim 1, wherein said static image specifying means is a freeze switch.

3. A static-image signal generation apparatus as claimed in claim 1, wherein said image storage/record means is a memory means in which image signals corresponding to the smallest movement amount detected by said minimum value detection means are stored.

4. A static-image signal generation apparatus as claimed in claim 1, further comprising a memory controlling means for controlling to store image signals input to said memory means and for controlling to read out image signals stored in the memory means.

5. A static-image signal generation apparatus as claimed in claim 1, wherein said detection time setting means performs fuzzy processing such that the larger the movement amount detected by said movement detection means the lengthier said detection time is set.

6. A static-image signal generation apparatus as claimed in claim 1, wherein said detection time setting means performs fuzzy processing such that the larger the gradient amount detected by said gradient detection means the lengthier said detection time is set.

7. A static-image signal generation apparatus as claimed in claim 1, wherein said detection time setting means, actuated by said detection time determined by said fuzzy inference means as well as said static image specifying signal, includes a second detection time setting means that forcibly terminates the operation of the minimum value detection by means of said minimum value detection means after a lapse of a fixed time.

8. A static-image signal generation apparatus as claimed in claim 1, wherein said detection time setting means includes a comparison means for comparing said detection time determined by said fuzzy inference means with a preset threshold value and forcibly terminates the operation of the minimum value detection by means of said minimum value detection means when said detection time is below said threshold value.

9. A static-image signal generation apparatus as claimed in claim 1, wherein said movement detection means includes a subtraction means for generating difference signals between a plurality of image signals of images photographed at different times and an absolute value generation means for obtaining the absolute value of the difference signal input from said subtraction means.

10. A static-image signal generation apparatus as claimed in claim 1, wherein said minimum value detection means includes a movement amount retaining means for retaining the movement amount detected by said movement detection means and a comparison means for comparing the movement amount detected by said movement detection means with the movement amount retained by said movement amount retaining means and for outputting an update signal for causing the movement amount detected by said movement detection means to be retained in said movement amount retaining means.

11. A static-image signal generation apparatus as claimed in claim 10, wherein said minimum value detection means includes a gate means for regulating the passage of said update signal output from said detection time setting means during said detection time and controls to store/record image signals corresponding to the movement amount such that the update signal is output by the update signal after passing through the gate means.

12. An endoscope apparatus, comprising:
an endoscope having a long and narrow insertion section, an illumination light emission means for emitting illumination light from the front end of said insertion section, an object optical system disposed on the front end of said insertion section for forming the image of an object, and a solid-state image pickup device for photoelectrically converting optical images based on said optical system;
drive signal generation means for outputting drive signals by which signals photoelectrically converted by said solid-state image pickup device are read out;
signal processing means for performing signal processing on signals output from said solid-state image pickup device;
monitor means on which standard video signals output from said signal processing means are displayed; and
static-image signal generation means having a movement detection means that detects the movement amount of said object image on the basis of the image signal of the input end or the output end of said signal processing means and that outputs a movement signal corresponding to said movement amount, a gradient detection means that detects the gradient of the movement amount on the basis of said movement signal output from said movement detection means, a minimum value detection means that detects the minimum value of a movement amount on the basis of said movement signal output from said movement detection means, a static-image specifying means that outputs a static-image specifying signal specifying a static image, a detection time setting means, actuated by said static-image specifying signal, that sets a detection time for the minimum value detection by means of said minimum value detection means by using a fuzzy inference means as factors for inferring the outputs of said movement detection means and said gradient detection means, and an image storage/record means for retaining image signals corresponding to the smallest movement amount detected by said minimum value detection means within said detection time as a static image.

13. An endoscope apparatus as claimed in claim 12, wherein said illumination light emission means is a frame sequence light emission means that chronologically emits illumination light of different wavelengths.

14. An endoscope apparatus as claimed in claim 12, wherein said solid-state image pickup device is provided with a color filter for color separation in the front of its photoelectric conversion surface.

15. A static-image signal generation method, comprising the steps of:
detecting the movement amount of an image on the basis of input image signals in correspondence with an object image;
detecting the gradient of a movement amount on the basis of a signal corresponding to the movement amount output in said movement detection step;
detecting the minimum value of said movement amount on the basis of a signal corresponding to said movement amount, the step of which is actuated by a static-image specifying signal;
setting a detection time for the minimum value detection in said minimum value detection step by fuzzy inference, as factors for fuzzy-inferring signals output in both said movement detection step and said gradient detection step; and
storing/recording image signals corresponding to the smallest movement amount detected in said minimum value detection step within said detection time as a static image.

16. A static-image signal generation method as claimed in claim 15, wherein in said detection time setting step, inference is made such that the larger the movement amount detected in said movement detection step, the lengthier said detection time is set.

17. A static-image signal generation method as claimed in claim 15, wherein in said detection time setting step, inference is made such that the larger the gradient amount detected in said gradient detection step, the lengthier said detection time is set.

18. A static-image signal generation method as claimed in claim 15, wherein in said detection time setting step, a process, actuated by said static-image specifying signal, by which said detection time is forcibly finished after a lapse of a fixed time, is performed in addition to the process by which said detection time is set by said fuzzy inference.

19. An endoscope apparatus, comprising:

an endoscope having a long and narrow insertion section, an illumination light emission means for emitting illumination light from the front end of said insertion section, an object optical system disposed on the front end of said insertion section for forming the image of an object, and a solid-state image pickup device for photoelectrically converting an optical image based on said optical system;

signal processing means for performing signal processing on signals outputted from said solid-state image pickup device;

monitor means on which standard video signals outputted from said signal processing means are displayed; and fuzzy inference means, contained in at least one of said illumination light emission means, said endoscope, said signal processing means, and said monitor means, for setting detection time in which said signals are processed.

* * * * *